(12) United States Patent
Mou et al.

(10) Patent No.: US 10,772,379 B2
(45) Date of Patent: Sep. 15, 2020

(54) DYNAMIC PRESSURE CONTROLLED AIR CUSHION DEVICE

(71) Applicant: Microjet Technology Co., Ltd., Hsinchu (TW)

(72) Inventors: Hao-Jan Mou, Hsinchu (TW); Li-Pang Mo, Hsinchu (TW); Shih-Chang Chen, Hsinchu (TW); Yung-Lung Han, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 323 days.

(21) Appl. No.: 16/001,257

(22) Filed: Jun. 6, 2018

(65) Prior Publication Data
US 2019/0000183 A1    Jan. 3, 2019

(30) Foreign Application Priority Data

Jul. 3, 2017   (TW) .............................. 106122226 A

(51) Int. Cl.
*A43B 13/20*        (2006.01)
*A43B 17/03*        (2006.01)
(Continued)

(52) U.S. Cl.
CPC .......... *A43B 13/203* (2013.01); *A43B 3/0005* (2013.01); *A43B 3/0015* (2013.01);
(Continued)

(58) Field of Classification Search
CPC ................ A61B 5/1036; A61B 5/1038; A61B 2562/0247; A61B 5/6807;
(Continued)

(56) References Cited

U.S. PATENT DOCUMENTS 5,179,792 A    1/1993  Brantingham
5,794,361 A    8/1998  Sadler
(Continued)

FOREIGN PATENT DOCUMENTS

CN    105188448 A    12/2015
CN    105962540 A    9/2016
(Continued)

OTHER PUBLICATIONS

Extended European Search Report, dated Dec. 4, 2018, for European Application No. 18176261.8.

*Primary Examiner* — Andre J Allen
(74) *Attorney, Agent, or Firm* — Birch, Stewart, Kolasch & Birch, LLP

(57) ABSTRACT

A dynamic pressure controlled air cushion device disposed on a bottom part of a shoe comprises a first air bag and a second air bag communicated with each other through an air passage, and the first air bag and the second air bag are respectively disposed corresponding to a front foot sole and a rear foot sole of a user. Through introducing the air into the first air bag by the first air pump and introducing the air into the second air bag by the second air pump, the first air bag and the second air bag are inflated, so as to increase a supporting force for the front foot sole and the rear foot sole of the user

16 Claims, 14 Drawing Sheets

(51) Int. Cl.
    A43B 13/18    (2006.01)
    A43B 3/00     (2006.01)
    A61B 5/107    (2006.01)
    A43B 13/12    (2006.01)
    A43B 13/10    (2006.01)

(52) U.S. Cl.
    CPC .......... *A43B 13/186* (2013.01); *A43B 13/206* (2013.01); *A43B 17/035* (2013.01); *A61B 5/1074* (2013.01); *A43B 13/10* (2013.01); *A43B 13/12* (2013.01)

(58) Field of Classification Search
    CPC . A61B 2562/046; A61B 5/112; A61B 5/4528; A61B 5/6892; A61B 5/0816; A61B 5/447; A61B 5/0002; A61B 5/0205; A61B 5/103; A61B 5/11; A61B 5/1126; A61B 5/113; A61B 2560/0214; A61B 5/02055; A61B 5/024; A61B 5/4818; A61B 5/0031; A61B 5/076; A61B 5/1116; A61B 5/1118; A61B 2034/102; A61B 2090/064; A61B 2562/02; A61B 2562/0219; A61B 2562/166; A61B 5/02438; A61B 5/1071; A61B 5/1074; A61B 5/1112; A61B 5/1117; A61B 5/1121; A61B 5/1123; A61B 5/224; A61B 5/4504; A61B 5/4533; A61B 5/486; A61B 5/6811; A61B 5/6812; A61B 5/6829; A61B 5/7242; A61B 5/742; A61B 10/00; A61B 2017/564; A61B 2034/105; A61B 2034/2055; A61B 2090/3983; A61B 2503/04; A61B 2503/08; A61B 2503/10; A61B 2503/40; A61B 2505/00; A61B 2505/09; A61B 2560/0242; A61B 2560/0285; A61B 2560/0412; A61B 2560/0456; A61B 2560/0468; A61B 2560/0475; A61B 2562/0252; A61B 2562/0266; A61B 2562/0271; A61B 2562/0276; A61B 2562/12; A61B 34/10; A61B 34/20; A61B 5/0015; A61B 5/0022; A61B 5/0053; A61B 5/0064; A61B 5/015; A61B 5/021; A61B 5/02444; A61B 5/031; A61B 5/04; A61B 5/055; A61B 5/107; A61B 5/1076; A61B 5/1077; A61B 5/1102; A61B 5/1113; A61B 5/1114; A61B 5/1115; A61B 5/1122; A61B 5/1124; A61B 5/1127; A61B 5/14532; A61B 5/14542; A61B 5/22; A61B 5/4023; A61B 5/412; A61B 5/442; A61B 5/45; A61B 5/4519; A61B 5/4523; A61B 5/4824; A61B 5/4833; A61B 5/4842; A61B 5/4848; A61B 5/4851; A61B 5/4866; A61B 5/6803; A61B 5/6806; A61B 5/681; A61B 5/6831; A61B 5/6833; A61B 5/6843; A61B 5/6846; A61B 5/6887; A61B 5/6891; A61B 5/6893; A61B 5/6895; A61B 5/6898; A61B 5/721; A61B 5/7225; A61B 5/7246; A61B 5/7264; A61B 5/7275; A61B 5/7405; A61B 5/743; A61B 5/7455; A61B 6/03; A61B 6/0407; A61B 90/36; A61B 90/361
    See application file for complete search history.

(56) References Cited

U.S. PATENT DOCUMENTS

| | | | |
|---|---|---|---|
| 2012/0255195 A1* | 10/2012 | Langvin | A43B 23/029 36/29 |
| 2014/0165427 A1* | 6/2014 | Molyneux | A43B 21/26 36/102 |
| 2017/0188885 A1* | 7/2017 | Banet | A61B 5/0537 |
| 2017/0188955 A1* | 7/2017 | Banet | A61B 5/02233 |
| 2017/0188956 A1* | 7/2017 | Banet | A61B 5/02141 |
| 2017/0188957 A1* | 7/2017 | Banet | G01G 19/52 |
| 2017/0188958 A1* | 7/2017 | Banet | A61B 5/002 |
| 2017/0188959 A1* | 7/2017 | Banet | A61B 5/7275 |
| 2017/0188960 A1* | 7/2017 | Banet | A61B 5/6892 |
| 2018/0177449 A1* | 6/2018 | Latey | A61B 5/486 |
| 2019/0000183 A1* | 1/2019 | Mou | A43B 3/0005 |
| 2020/0046071 A1* | 2/2020 | Henrichot | A43B 13/203 |
| 2020/0163411 A1* | 5/2020 | Molyneux | A43B 13/20 |
| 2020/0170343 A1* | 6/2020 | Bailly | A43B 13/203 |

FOREIGN PATENT DOCUMENTS

| | | |
|---|---|---|
| CN | 106072978 A | 11/2016 |
| KR | 10-0744646 B1 | 8/2007 |
| TW | 201610298 A | 3/2016 |
| TW | M541542 U | 5/2017 |
| WO | WO 94/05177 A1 | 3/1994 |
| WO | WO 01/78539 A2 | 10/2001 |
| WO | WO 2006/003635 A1 | 1/2006 |
| WO | WO 2014/099717 A1 | 6/2014 |

* cited by examiner

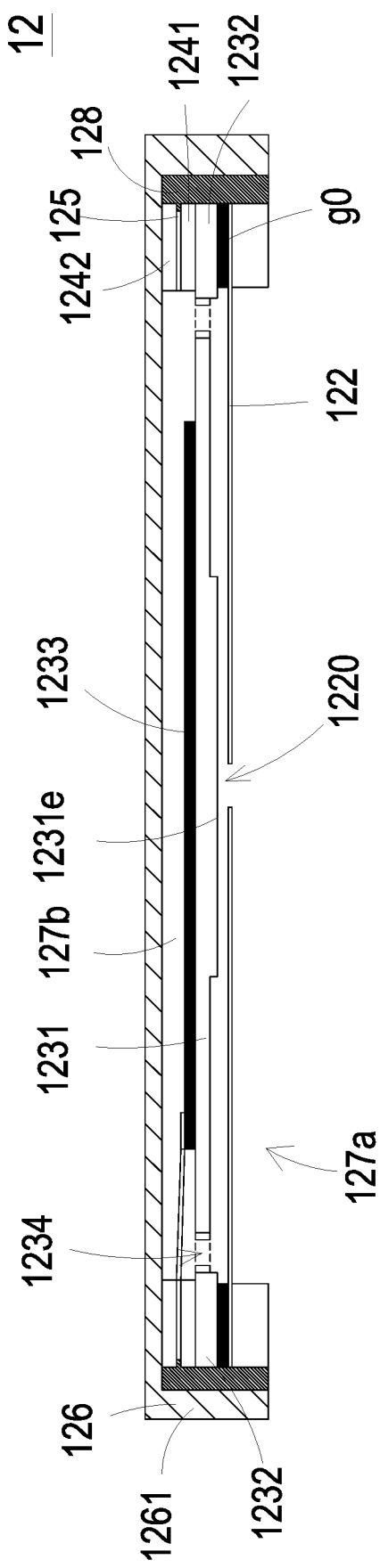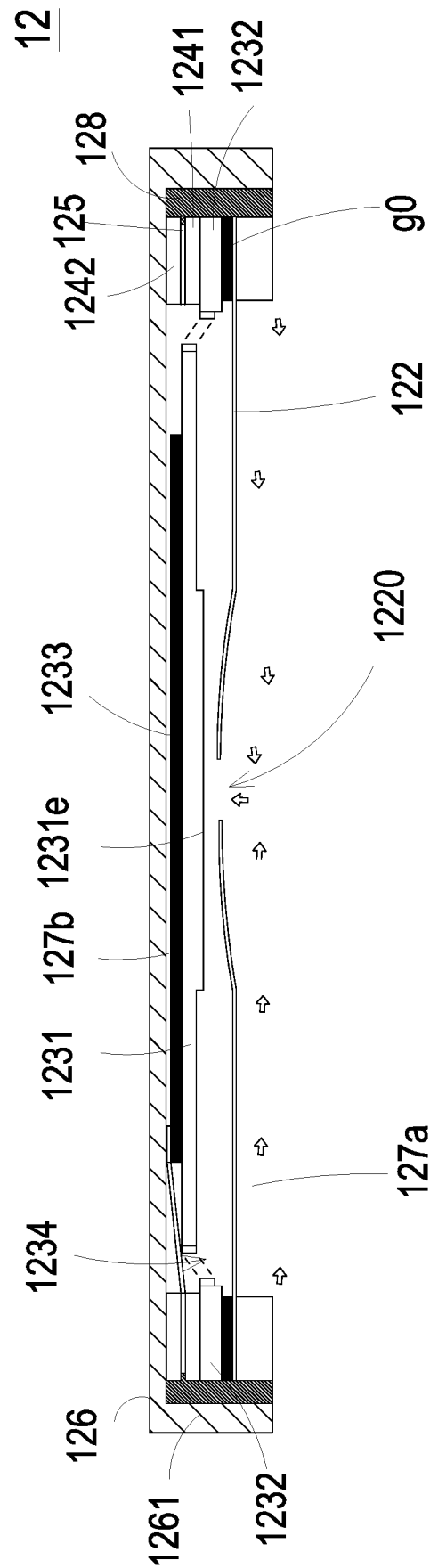
FIG. 8A
FIG. 8B

DYNAMIC PRESSURE CONTROLLED AIR CUSHION DEVICE

FIELD OF THE INVENTION

The present disclosure relates to a dynamic pressure controlled air cushion device, and more particularly to a dynamic pressure controlled air cushion device inflated with an air pump.

BACKGROUND OF THE INVENTION

Generally, the cushioning and supporting capacity of the soles are important to the shoes, especially sports shoes or work shoes. For example, when the cushioning capacity of the sole is insufficient, it is easily to cause foot pain or knee pain when the user exercises or works with wearing the shoes, and may lead to the occurrence of plantar fasciitis. When the supporting capacity of the sole is insufficient, it is easy to cause foot sprains to the user or damage to the shoes when the user exercises or works with wearing the shoes.

Most conventional shoes are filled with foam on the bottom parts, thereby providing the user's foot with supporting and cushioning capacity. Furthermore, depending on the shape of the user's foot or the way it exercise, foam with different densities may be correspondingly disposed on the specific position where the force is applied, thereby providing the user with a good shoe-wearing experience. However, after the foam is worn for a period of time, it is easily to cause the elasticity loss of the foam such that the cushioning and supporting capacity are lost. In addition, before customizing the foam of the sole according to the user's wearing habits, it is necessary to observe the user's habit of wearing shoes for a long time, and even to obtain the relevant information of the foot pressure through the testing apparatus. This process will result in waste of manufacturing cost, time and labor, which is very unfriendly to people having foot shapes of high arches or fallen arches, and it also leads to the possibility of danger while wearing.

Among the commercially available shoes, some of the shoes are provided with air cushions, pads, or leaf springs on the soles to provide cushioning and support. However, the pressure inside the air cushions or pads of those shoes cannot be adjusted according to user's wearing requirements, which is fail to meet the foot shapes and usage habits of each person and provide comfortable wear feeling.

Therefore, there is a need of providing a dynamic pressure controlled air cushion device to solve the drawbacks in prior arts, and be capable of adjusting the pressure of the sole and achieving comfort, cushioning and support.

SUMMARY OF THE INVENTION

An object of the present disclosure provides a dynamic pressure controlled air cushion device, so as to adjust the pressure of the sole and achieve the advantages of comfort, cushioning and supporting capacity.

In accordance with an aspect of the present disclosure, a dynamic pressure controlled air cushion device applied to a shoe is provided, and the shoe includes a bottom part. The dynamic pressure controlled air cushion device includes a first air bag disposed on the bottom part and disposed corresponding to a front foot sole of a user, a second air bag disposed on the bottom part and disposed corresponding to a rear foot sole of the user, an air passage communicated between the first air bag and the second air bag, a first air pump disposed and enclosed in the air passage, a second air pump disposed and enclosed in the air passage, a first sensor disposed on the bottom part and disposed adjacent to the first air bag, a second sensor disposed on the bottom part and disposed adjacent to the second air bag; and a control module electrically connected with the first air pump, the second air pump, the first sensor and the second sensor. When the first sensor senses that a force exerted by the front foot sole of the user is larger than a specific first load value interval, the first sensor sends a first sensing signal to the control module, and the control module enables the first air pump according to the first sensing signal, so that air is introduced into the first air bag by the first air pump, and the first air bag is inflated to increase a supporting force for the front foot sole of the user. When the second sensor senses that a force exerted by the rear foot sole of the user is larger than a specific second load value interval, the second sensor sends a second sensing signal to the control module, and the control module enables the second air pump according to the second sensing signal, so that the air is introduced into the second air bag by the second air pump, and the second air bag is inflated to increase a supporting force for the rear foot sole of the user.

The above contents of the present disclosure will become more readily apparent to those ordinarily skilled in the art after reviewing the following detailed description and accompanying drawings, in which:

BRIEF DESCRIPTION OF THE DRAWINGS

FIG. 8A to FIG. 8D schematically illustrate the actions of the first air pump according to an embodiment of the present disclosure.

DETAILED DESCRIPTION OF THE PREFERRED EMBODIMENT

The present disclosure will now be described more specifically with reference to the following embodiments. It is noted that the following descriptions of preferred embodiments of this invention are presented herein for purpose of illustration and description only. It is not intended to be exhaustive or to be limited to the precise form disclosed.

Figure 1:
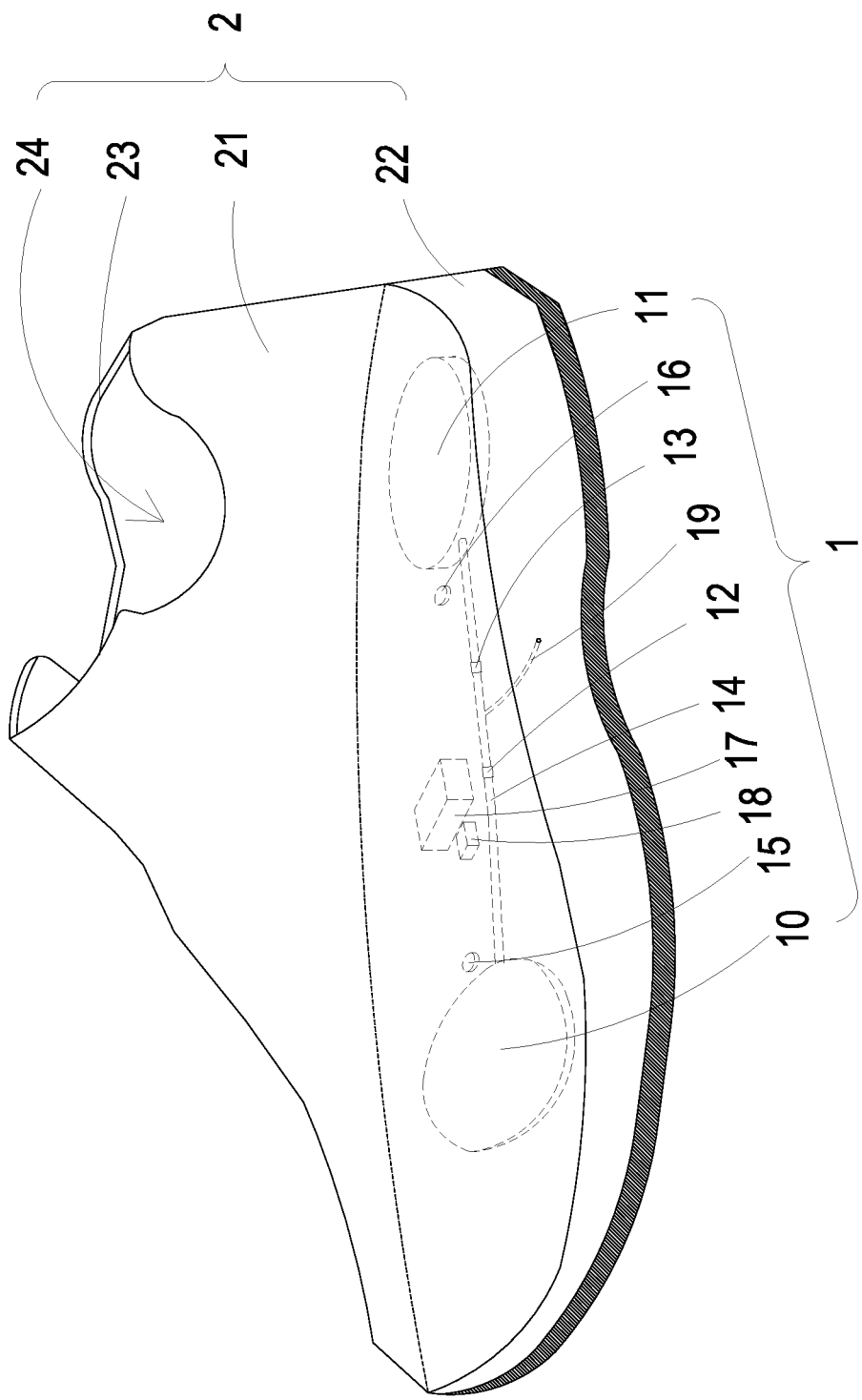
FIG. 1 schematically illustrates the structure of the dynamic pressure controlled air cushion device applied to the sneaker according to an embodiment of the present disclosure.
Figure 2:
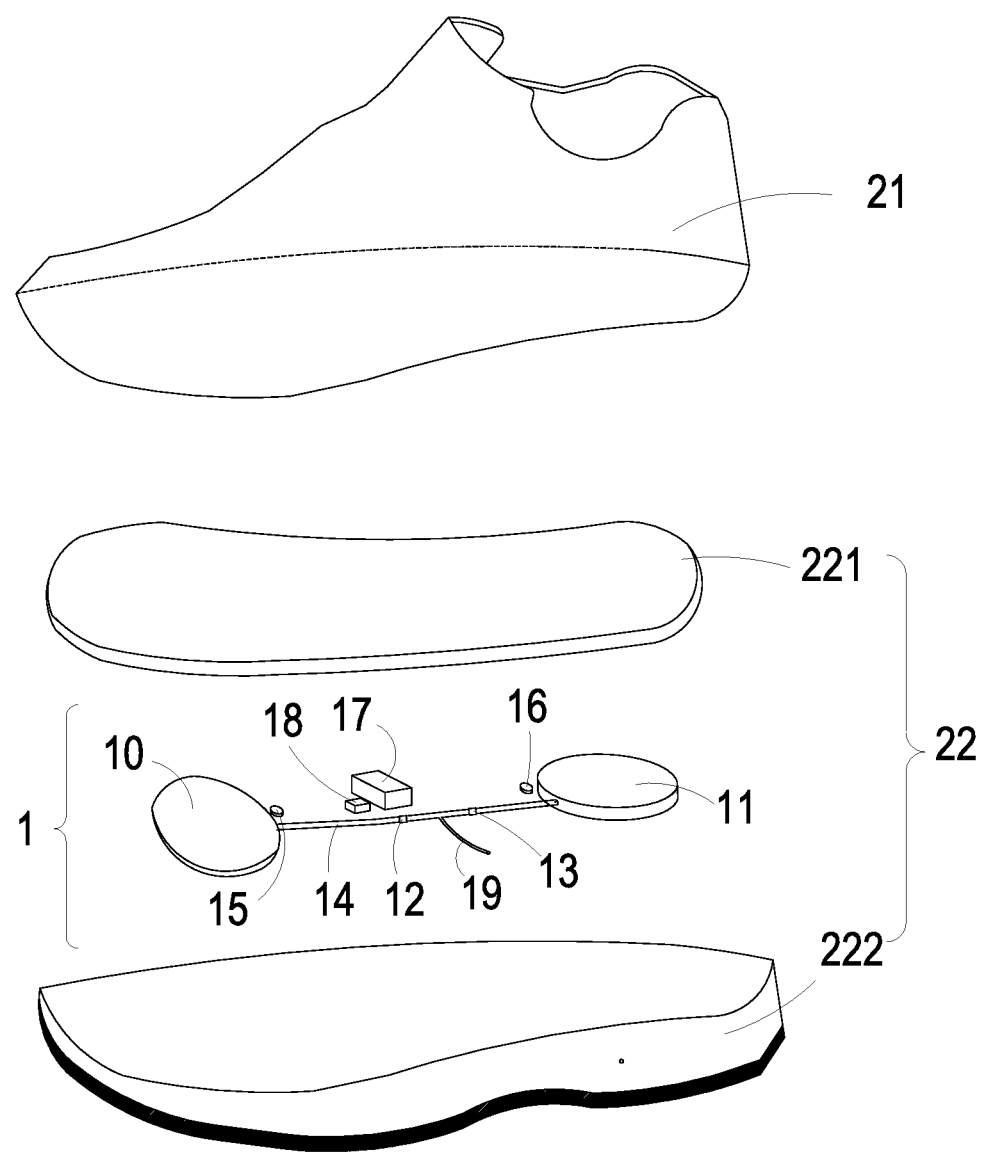
FIG. 2 schematically illustrates the exploded structure of the dynamic pressure controlled air cushion device applied to the sneaker in FIG. 1.

Please refer to FIG. 1 and FIG. 2. FIG. 1 schematically illustrates the structure of the dynamic pressure controlled air cushion device applied to the shoe according to an embodiment of the present disclosure. FIG. 2 schematically illustrates the exploded structure of the dynamic pressure controlled air cushion device applied to the shoe in FIG. 1. The dynamic pressure controlled air cushion device 1 can be applied to various kinds of shoes, such as sneakers, sandals, or high heels, but not limited herein. As shown in FIG. 1, the dynamic pressure controlled air cushion device 1 is exemplarily applied to a sneaker 2 for illustration purpose. The sneaker 2 includes a shoe body 21 and a bottom part 22. The shoe body 21 is connected to the bottom part 22 to define an opening 23 and a wear space 24, and one of the user's feet can be inserted into the wear space 24 through the opening 23. As shown in FIG. 2, the bottom part 22 of the sneaker 2 further includes an insole 221 and the sole 222. In this embodiment, the dynamic pressure controlled air cushion device 1 is embedded in the sole 222 and covered with the insole 221 thereon, in order to prevent the user's foot from directly stepping on the elements of the dynamic pressure controlled air cushion device 1.

Figure 3:
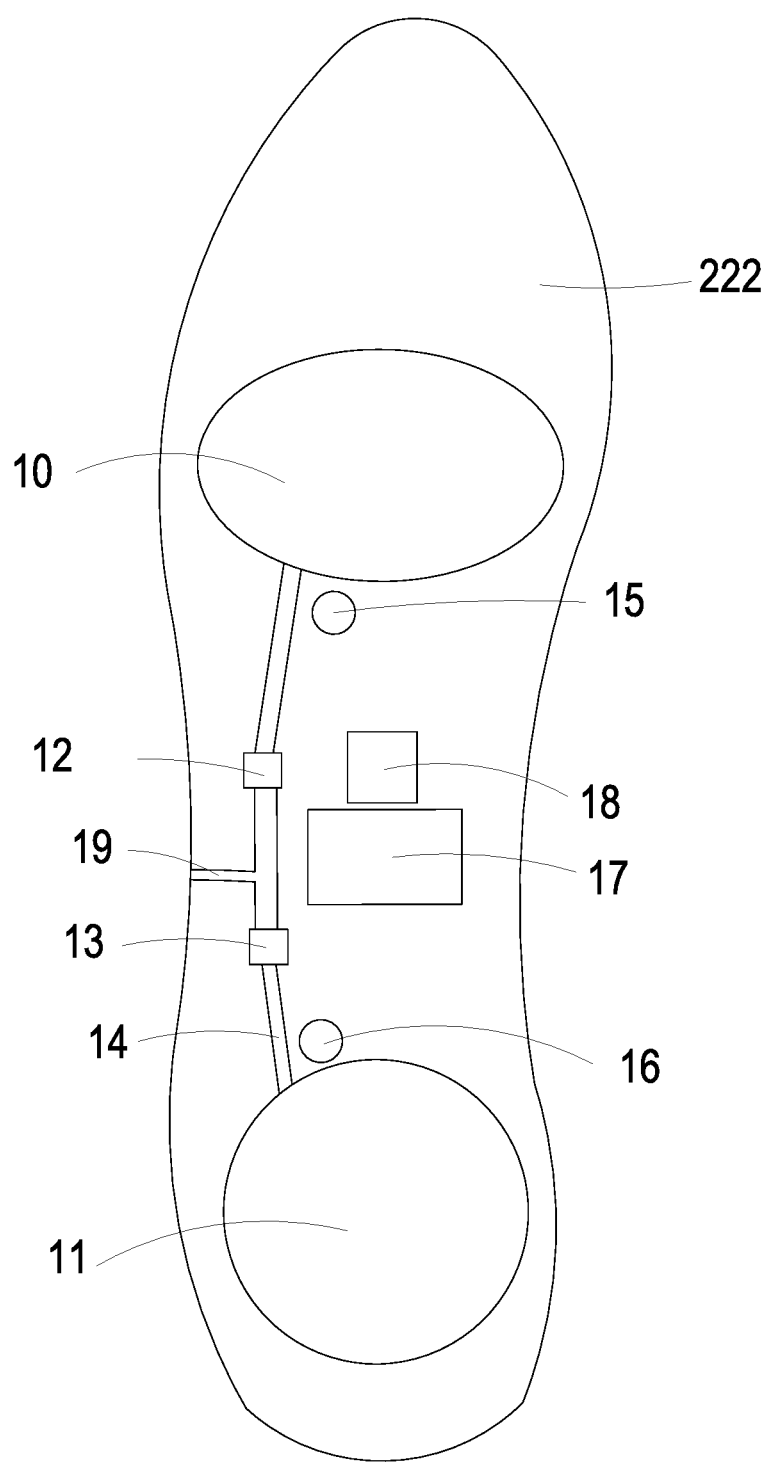
FIG. 3 schematically illustrates the top view from the bottom of the dynamic pressure controlled air cushion device applied to the sneaker in FIG. 1.

Please refer to FIG. 1 and FIG. 3. FIG. 3 schematically illustrates the top view from the bottom of the dynamic pressure controlled air cushion device applied to the sneaker in FIG. 1. As shown in FIG. 1 and FIG. 3, the dynamic pressure controlled air cushion device 1 includes a first air bag 10, a second air bag 11, a first air pump 12, a second air pump 13, an air passage 14, a first sensor 15, a second sensor 16, a control module 17, a battery module 18 and an external passage 19. The first air bag 10 and the second air bag 11 are made of inflated and expanded elastic materials, such as Polyurethane (PU), but not limited herein. The first air bag 10 and the second air bag 11 are disposed on the bottom part 22 of the sneaker 2. The first air bag 10 is disposed corresponding to the front foot sole of the user (i.e., the metatarsal bone portion of the user's sole of the foot), and the second air bag 11 is disposed corresponding to the rear foot sole of the user (i.e., the heel portion of the user's sole of the foot). In this embodiment, the air passage 14 is a hollow communication passage, and the air passage 14 is communicated between the first air bag 10 and the second air bag 11, thereby enabling air transmission between the first air bag 10 and the second air bag 11. The first air pump 12 and the second air pump 13 are disposed and enclosed in the air passage 14. The first air pump 12 is disposed adjacent to the first air bag 10, and the second air pump 13 is disposed adjacent to the second air bag 11, but not limited thereto. The air is introduced into the first air bag 10 by the first air bump 12, so that the first air bag 10 is inflated and expanded, thereby providing the front foot sole of the user with cushioning and supporting force. The air is introduced into the second air bag 11 by the second air pump 13, so that the second air bag 11 is inflated and expanded, thereby providing the rear foot sole of the user with cushioning and supporting force. In this embodiment, the air passage 14 is communicated with an environment outside the sneaker 2 through the external passage 19, but not limited herein. More specifically, owing to the installation of the external passage 19, the first air pump 12 is able to pump the air from the environment outside the sneaker 2 into the first air bag 10, and the second air pump 13 is able to pump the air from the environment outside the sneaker 2 into the second air bag 11.

Please refer to FIG. 1 and FIG. 3. As shown in FIG. 1 and FIG. 3, the first sensor 15 and the second sensor 16 of this embodiment are disposed on the bottom part 22, both of which are used to sense whether the foot of the user puts into the wear space 24 of the sneaker 2. The first sensor 15 is disposed adjacent to the first air bag 10 to sense the force applied by the user's front foot sole, and the second sensor 16 is disposed adjacent to the second air bag 11 to sense the force applied by the user's rear foot sole. Therefore, the exertion of the force applied by the user's front foot sole and rear foot sole is judged by sensing the weight exerted on the first sensor 15 and the second sensor 16 by the user's foot. In this embodiment, the control module 17 is electrically connected to the first air pump 12, the second air pump 13, the first sensor 15 and the second sensor 16 to receive signals and drive the elements of the dynamic pressure controlled air cushion device 1 to operate. In this embodiment, the battery module 18 is disposed adjacent to the control module 17 for supplying electrical energy to the control module 17, but not limited thereto.

Figure 4A:
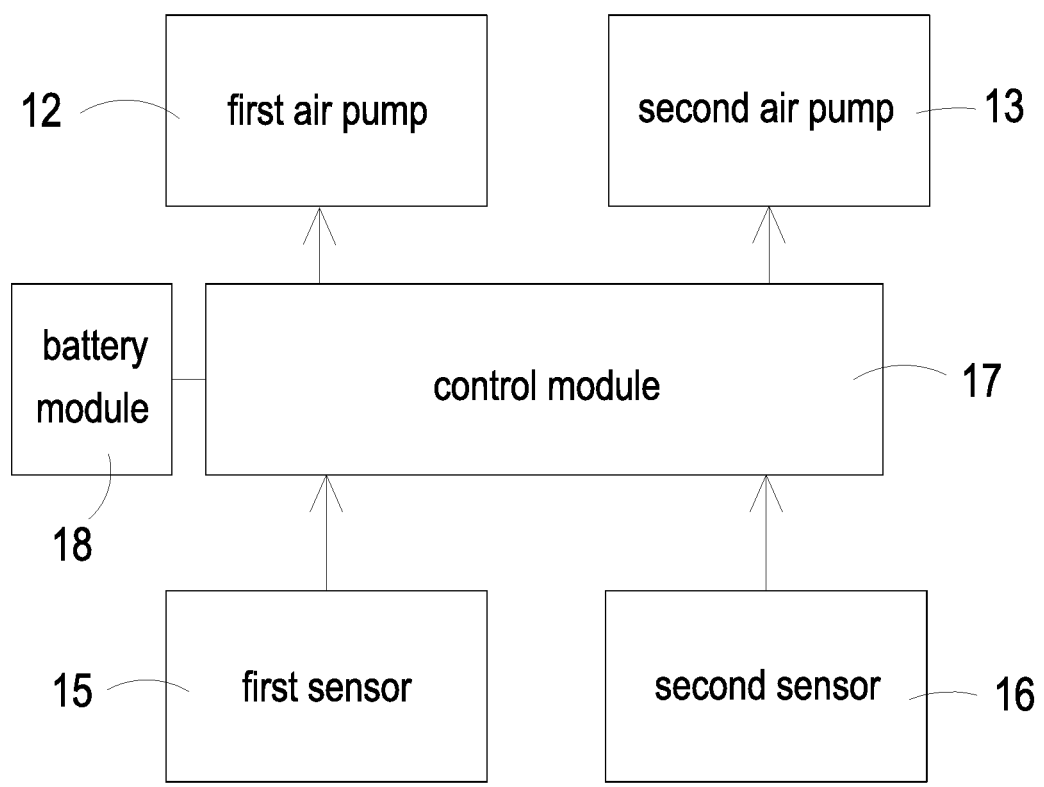
FIG. 4A schematically illustrates the architecture of the dynamic pressure controlled air cushion device according to an embodiment of the present disclosure.
Figure 4B:
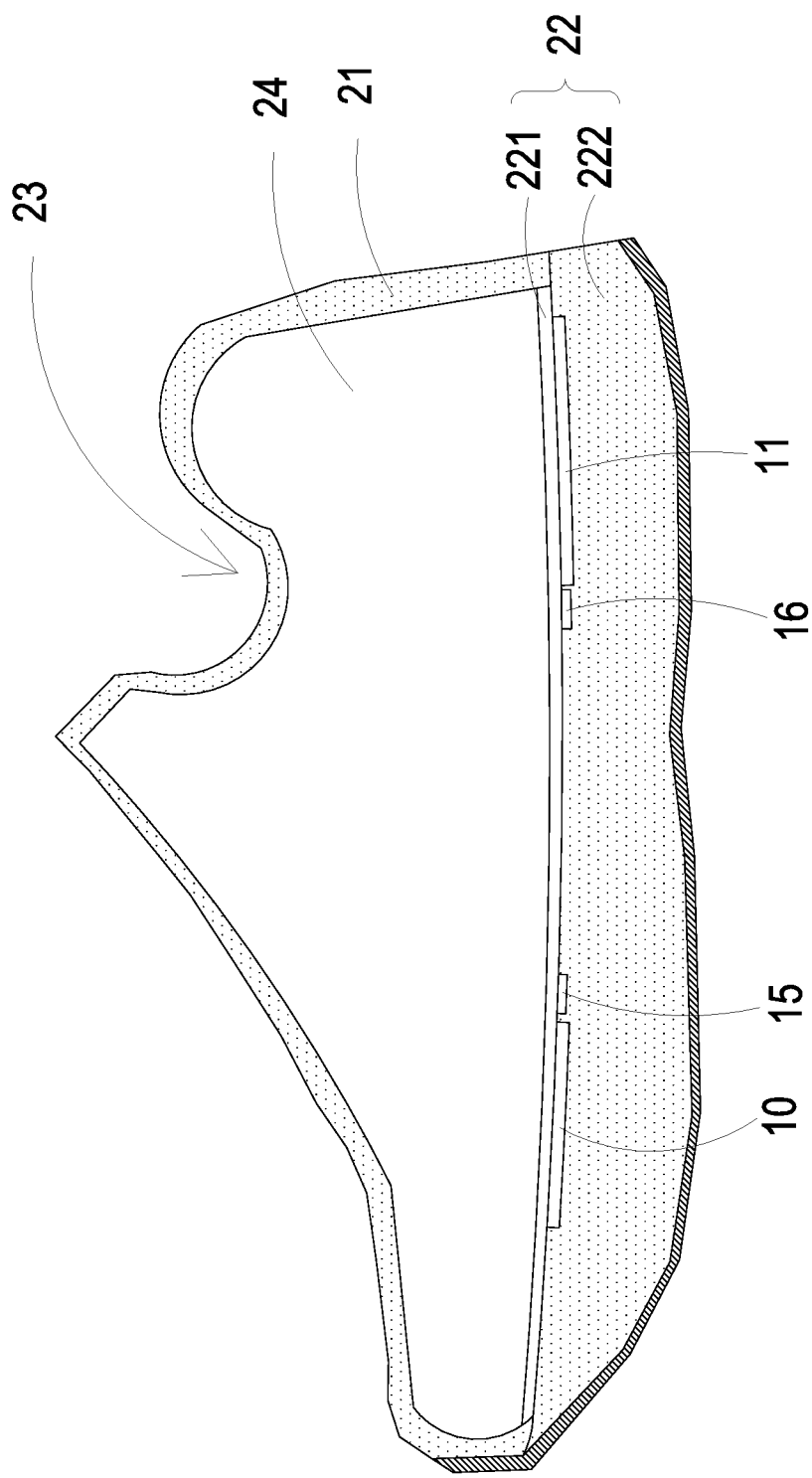
FIG. 4B schematically illustrates the cross-sectional view of the structure of the dynamic pressure controlled air cushion device applied to the sneaker in FIG. 4A.
Figure 4C:
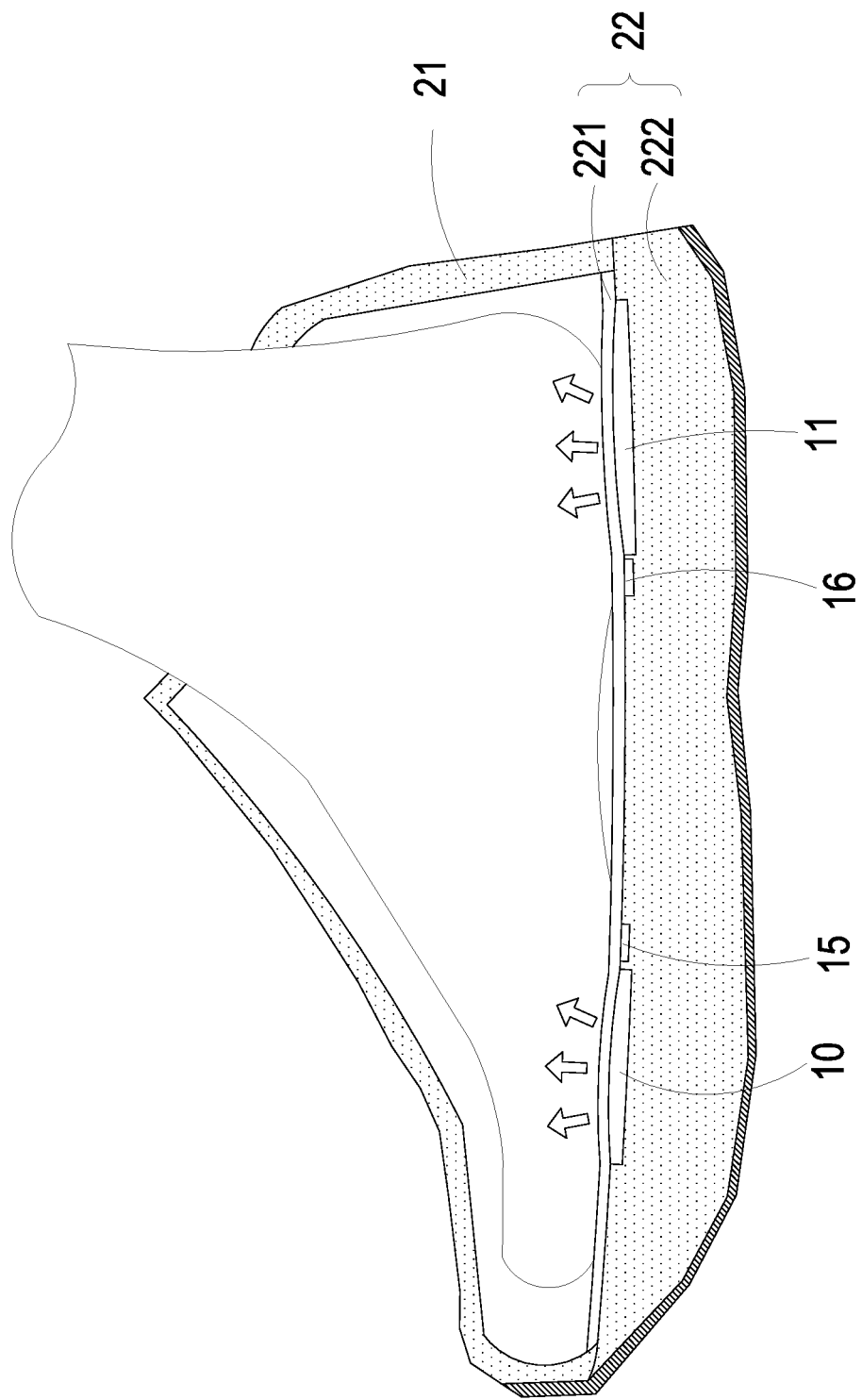
FIG. 4C schematically illustrates the shoe in FIG. 4B, in which the sneaker is worn.

Please refer to FIG. 3 to FIG. 4C. FIG. 4A schematically illustrates the architecture of the dynamic pressure controlled air cushion device according to an embodiment of the present disclosure. FIG. 4B schematically illustrates the cross-sectional view of the structure of the dynamic pressure controlled air cushion device applied to the sneaker in FIG. 4A. FIG. 4C schematically illustrates the shoe in FIG. 4B, in which the sneaker is worn. As shown in FIG. 4B, when the first sensor 15 and the second sensor 16 do not sense a force, the first air bag 10 and the second air bag 12 are in an uninflated initial state. As shown in the FIG. 4A, when the first sensor 15 senses that a force exerted by the front foot sole of the user is larger than a specific first load value interval, the first sensor 15 sends a first sensing signal to the control module 17, and the control module 17 enables the first air pump 12 according to the first sensing signal, so that the air is introduced into the first air bag 10 by the first air pump 12, and the first air bag 10 is inflated to increase a supporting force for the front foot sole of the user. When the second sensor 16 senses that a force of the rear foot sole of the user is larger than a specific second load value interval, the second sensor 16 sends a second sensing signal to the control module 17, and the control module 17 enables the second air pump 13 according to the second sensing signal, so that the air is introduced into the second air bag 11 by the second air pump 13, and the second air bag 11 is inflated to increase a supporting force for the rear foot sole of the user. As shown in FIG. 4C, by operating in the manner described above, both the first air bag 10 and the second air bag 11 can be independently inflated to increase the pressure, thereby providing the user's foot with sufficient supporting force and cushioning capacity, avoiding imbalance of the front foot sole and the rear foot sole, and improving the comfort of overall wearing significantly. In addition, the first sensor 15 and the second sensor 16 may sense different manners of force exertion from different users and adjust the supporting force provided by the first air bag 10 and the second air bag 11, thereby adjusting to the best condition for the user. In this embodiment, the specific first load value interval and the specific second load value interval are preset (default values), and the user may reset it for the most comfortable foot feeling or according to the distribution of the foot force measured by professional instruments, but not limited thereto.

As described above, in this embodiment, when the first sensor 15 senses that the force exerted by the front foot sole of the user reaches the specific first load value interval, the first sensor 15 sends a first disabling signal to the control module 17, and the control module 17 controls the first air pump 12 to stop operating according to the first disabling signal, so that the first air pump 12 stops inflating the first air bag 10, and the pressure inside the first air bag 10 can be maintained at the specific first load value interval. When the second sensor 16 senses that the force exerted by the rear foot sole of the user reaches the specific second load value interval, the second sensor 16 sends a second disabling signal to the control module 17, and the control module 17 controls the second air pump 13 to stop operating according to the second disabling signal, so that the second air pump 13 stops inflating the second air bag 11, and the pressure inside the second air bag 11 can be maintained at the specific second load value interval. By operating in the manner described above, the pressure inside the first air bag 10 and the second air bag 11 is stably maintained, thereby ensuring that the dynamic pressure controlled air cushion device 1 can stably provide appropriate supporting force to the user's foot, preventing the first air pump 12 and the second air pump 13 from operating ceaselessly and resulting in a shorter service life, and avoiding continuous inflation, which may cause damage to the first air bag 10 and the second air bag 11 because of excessive internal pressure.

In this embodiment, the first air pump 12 further includes a first non-return valve (not shown), which is a switchable valve structure. When the first air pump 12 stops operating, the air passage 14 is closed by the first non-return valve to prevent the air in the first air bag 10 from backflow. When the first sensor 15 senses that the force exerted by the front foot sole of the user is less than the specific first load value interval, the first sensor 15 sends a first decompressing signal to the control module 17, and the control module 17 enables the first non-return valve according to the first decompressing signal, so that the first non-return valve is opened, the air is discharged from the first air bag 10, and the first air bag 10 exhausts to decrease the supporting force of the front foot sole for the user. In this embodiment, the second air pump 13 further comprises a second non-return valve (not shown), which is a switchable valve structure. When the second air pump 13 is stopped operating, the air passage 14 is closed by the second non-return valve to prevent the air in the second air bag 11 from backflow. When the second sensor 16 senses that the force exerted by the rear foot sole of the user is less than the specific second load value interval, the second sensor 16 sends a second decompressing signal to the control module 17, and the control module 17 enables the second non-return valve according to the second decompressing signal, so that the second non-return valve is opened, the air is discharged from the second air bag 11, and the second air bag 11 exhausts to decrease the supporting force for the rear foot sole of the user. Owing to the installation of the first non-return valve and the second non-return valve, backflow of the air inside the first air bag 10 and the second air bag 11 is avoided, so that the first air bag 10 and the second air bag 11 can provide stable supporting force to the user's foot. Furthermore, when the supporting force provided by the first air bag 10 and the second air bag 11 is too large, the first air bag 10 and the second air bag 11 are able to exhaust and decompress under control, so that appropriate supporting force is provided from the first air bag 10 and the second air bag 11 to the user's foot, thereby improving comfort when wearing the sneaker 2.

In this embodiment, the first sensor 15 is a load sensor, and the first sensor 15 is disposed adjacent to the first air bag 10, but not limited herein. The first sensor 15 sends the first enabling signal or the first disabling signal to the control module 17 according to changes of the force exerted on the first sensor 15 by the user's front foot sole, thereby enabling the first air pump 12 to operate or stop operating. In this embodiment, the second sensor 16 is a load sensor, the second sensor 16 is disposed adjacent to the second air bag 11, but not limited thereto. The second sensor 16 sends the second enabling signal or the second disabling signal to the control module 17 according to changes of the force exerted on the second sensor 16 by the user's front foot sole, thereby enabling the second air pump 13 to operate or stop operating.

In some embodiments, the first sensor 15 can be but not limited to an air pressure sensor, and the first sensor 15 is communicated with an interior of the first air bag 10, so as to sense the changes of air pressure generated by the front foot sole of the user in the first air bag 10, and accordingly send the first enabling signal or the first disabling signal to the control module 17 to drive the first air pump 10 to operate or to stop operating. In this embodiment, the second sensor 16 can be but not limited to an air pressure sensor, and the second sensor 16 is communicated with an interior of the second air bag 11, so as to sense the changes of air pressure generated by the rear foot sole of the user in the second air bag 11, and accordingly send the second enabling signal or the second disabling signal to the control module 17 to drive the second air pump 13 to operate or to stop operating.

In some embodiments, the dynamic pressure controlled air cushion device 1 further includes a manual adjustment device (not shown), which is a button, a switch or a remote control device. The manual adjustment device is disposed on the surface of the sneaker 2 and electrically connected to the control module 17, but not limited herein. The user can switch the manual adjustment device on and off to set the range of the specific first load value interval and the specific second load value interval, thereby allowing the user to adjust the supporting force provided by the first air bag 10 and the second air bag 11 whenever and wherever the user feels discomfort.

In some embodiments, the control module 17 further includes a wireless signal transmission and receiving unit (not shown) for transmitting a data signal to a control computer or a portable electronic device. The wireless signal transmission and receiving unit may transmit signals wirelessly via infrared, Bluetooth or WIFI, but not limited thereto. The data signal is related to the force exerted by the fore foot sole and the rear foot sole of the user and the supporting force provided by the first air bag 10 and the second air bag 11. When the control computer or the portable electronic device receives the data signal, the user can monitor the force conditions provided by the fore foot sole and the rear foot sole and details of the supporting force provided by the dynamic pressure controlled air cushion device 1 through controlling the computer or the portable electronic device. Also, the user can adjust the specific first load value interval, the specific second load value interval, and the supporting force provided by the first air bag 10 and the second air bag 11 by controlling the computer or the portable electronic device, thereby enabling the user to adjust to a comfortable state whenever and wherever the user feels uncomfortable. In some embodiments, the wireless signal transmission and receiving unit of the control module 17 is used to transmit data signals to another dynamic pressure controlled air cushion device (not shown), or receive the data signals sent by another dynamic pressure controlled air cushion device. For example, the dynamic pressure controlled air cushion device 1 of this embodiment is installed on the left foot (not shown) of the sneaker 2, and another dynamic pressure controlled air cushion device is installed on the right foot (not shown) of the sneaker 2. When the another dynamic pressure controlled air cushion device transmits the data signal to the dynamic pressure controlled air cushion device 1, the wireless signal transmission and receiving unit of the control module 17 of the dynamic pressure controlled air cushion device 1 receives the data signal, and the control module 17 adjusts the specific first load value interval, the specific second load value interval, and the supporting force provided by the first air bag 10 or the second air bag 11 according to the data signal, so that an information carried by the data signal enables the dynamic pressure controlled air cushion device 1 to set parameters described above (e.g., the specific first load value interval and the specific second load value interval) to the same values as those in the another dynamically controlled air cushion device, thereby balancing the difference in exerted forces between the left foot and the right foot when wearing the sneakers 2 and improving the comfort of overall wearing.

Figure 5A:
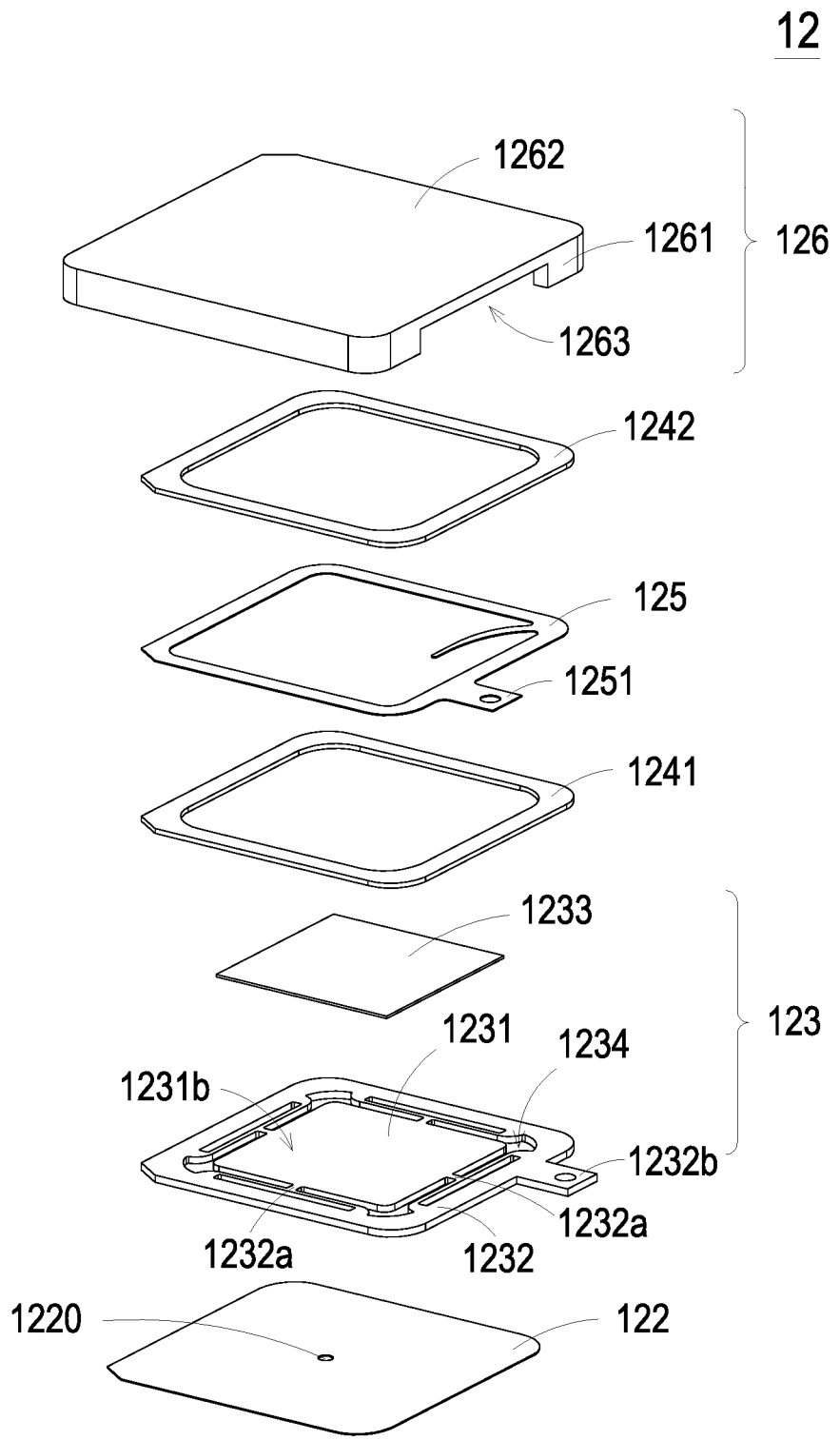
FIG. 5A schematically illustrates the front view of the exploded structure of the first air pump according to an embodiment of the present disclosure.
Figure 5B:
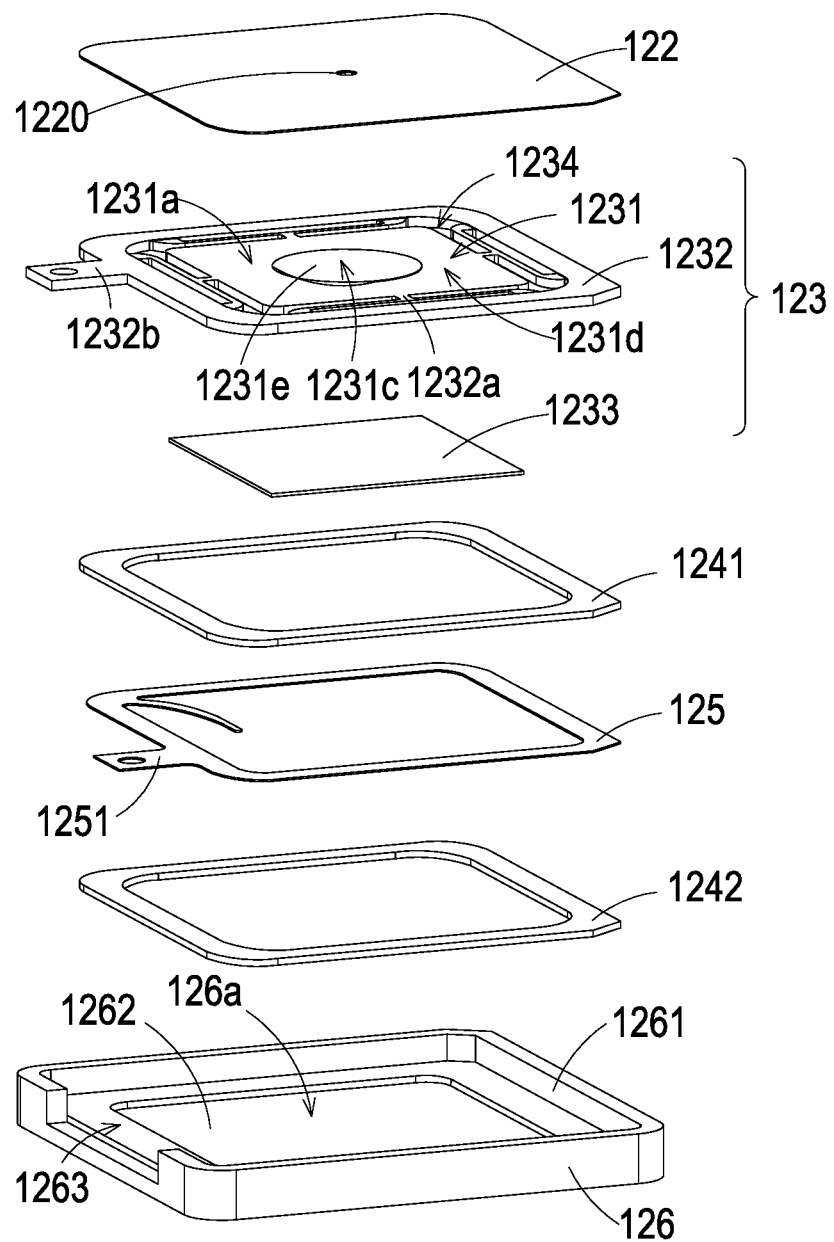
FIG. 5B schematically illustrates the rear view of the exploded structure of the first air pump according to an embodiment of the present disclosure.

Please refer to FIGS. 5A and 5B. FIG. 5A schematically illustrates the front view of the exploded structure of the first air pump according to an embodiment of the present disclosure. FIG. 5B schematically illustrates the rear view of the exploded structure of the first air pump according to an embodiment of the present disclosure. In this embodiment, structures of the first air pump 12 and the second air pump 13 are the same, so do their actuation modes. Accordingly, the internal structure of the second air pump 13 will not be further described in detail, but not limited herein. In this embodiment, the first air pump 12 is a piezoelectric air pump for driving the flow of the air. As shown in FIGS. 5A and 5B, the first air pump 12 of the present disclosure includes a resonance plate 122, a piezoelectric actuator 123 and a cover plate 126. The resonance plate 122 is spatially corresponding to the piezoelectric actuator 123. The resonance plate 122 includes a central aperture 1220 disposed on the central area of the resonance plate 122, and the resonance plate 122 includes a movable part near the central aperture 1220, but not limited thereto. The piezoelectric actuator 123 includes a suspension plate 1231, an outer frame 1232 and a piezoelectric element 1233. The suspension plate 1231 can be but not limited to a square suspension plate with a bulge 1231e, and the suspension plate 1231 includes a central portion 1231c and a peripheral portion 1231d. When a voltage is applied to the piezoelectric element 1233, the suspension plate 1231 is subjected to a bending vibration from the central portion 1231c to the peripheral portion 1231d. The outer frame 1232 is arranged around the outside of the suspension plate 1231 and includes at least one bracket 1232a and a conducting pin 1232b, but not limited thereto. Each bracket 1232a includes two ends connected between the suspension plate 1231 and the outer frame 1232 for providing an electrically supporting. The conducting pin 1232b protrudes outwardly from the outer frame 1232 for an electrically external connection. The piezoelectric element 1233 is attached to a second surface 1231b of the suspension plate 1231. The length of a side of the piezoelectric element 1233 is equal to or less than the length of a side of the suspension plate 1231, so as to receive the applied voltage and generate the deformation to drive the bending vibration of the suspension plate 1231. The cover plate 126 includes at least one sidewall 1261, a bottom plate 1262 and an opening portion 1263. The sidewalls 1261 are arranged around the periphery of the bottom plate 1262 and protrudes therefrom, so as to define an accommodation space 126a by the sidewalls 1261 and the bottom plate 1262 collaboratively. The resonance plate 122 and the piezoelectric actuator 123 are accommodated within the accommodation space 126a. The opening portion 1263 is disposed on the sidewall 1261 so that the conducting pin 1232b of the outer frame 1232 passes through the opening portion 1263 and protrudes out of the cover plate 126. It aids the conducting pin 1232b to connect to an external power, but the present disclosure is not limited thereto.

In this embodiment, the first air pump 12 of the present disclosure further includes a first insulation plate 1241, a second insulation plate 1242 and a conducting plate 125, but not limited thereto. The first insulation plate 1241 and the second insulation plate 1242 are disposed on the top and the bottom of the conducting plate 125, respectively, and have the profiles substantially matching the profile of the outer frame 1232 of the piezoelectric actuator 123. The first insulation plate 1241 and the second insulation plate 1242 can be made of an insulating material, for example but not limited to a plastic material, for providing insulating efficacy. The conducting plate 125 is made of an electrically conductive material, for example but not limited to a metallic material, for providing electrically conducting efficacy. The conducting plate 125 has its profile substantially matching the profile of the outer frame 1232 of the piezoelectric actuator 123, but the present disclosure is not limited thereto. Moreover, the conducting plate 125 may have a conducting pin 1251 used for electrically external conduction. Being similar to the conducting pin 1232b of the outer frame 1232, the conducting pin 1251 passes through the opening portion 1263 of the cover plate 126 and protrudes out of the cover plate 126 for electrically connecting to the control module 17.

Figure 6A:
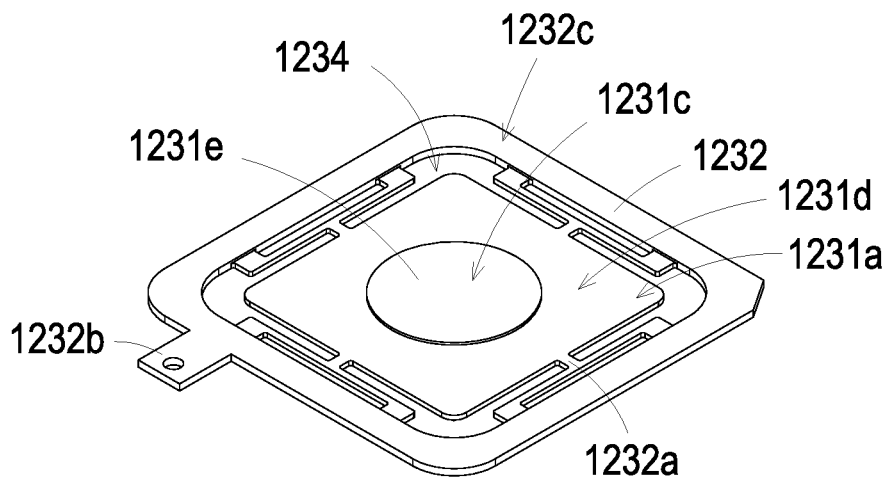
FIG. 6A schematically illustrates the front view of the structure of the piezoelectric actuator of FIGS. 5A and 5B.
Figure 6B:
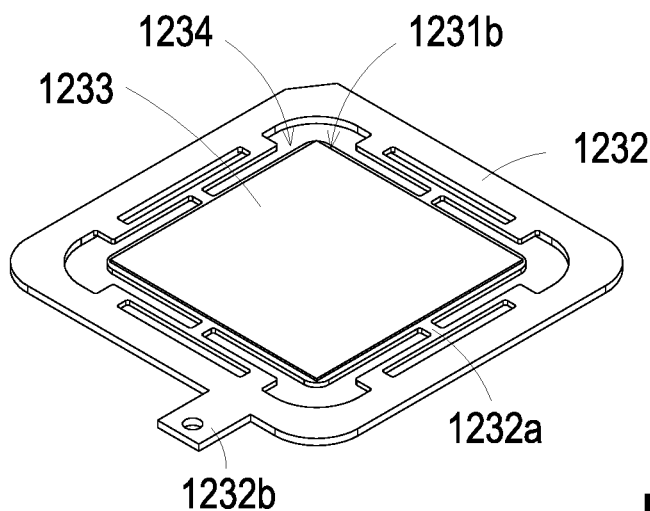
FIG. 6B schematically illustrates the rear view of the structure of the piezoelectric actuator of FIGS. 5A and 5B.
Figure 6C:
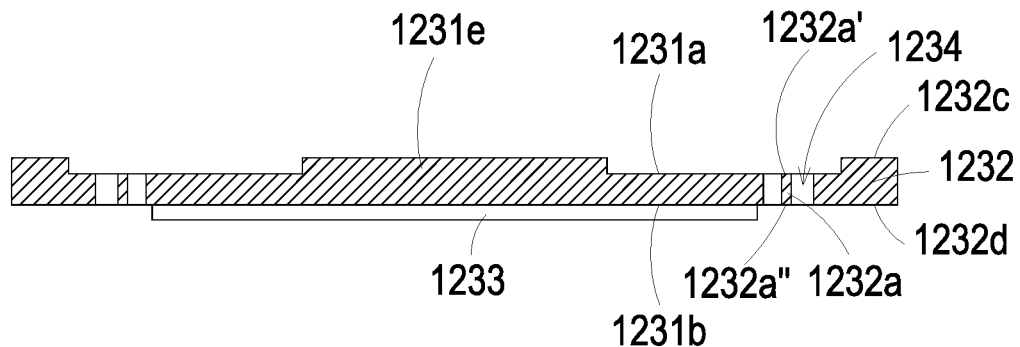
FIG. 6C schematically illustrates the cross-sectional view of the structure of the piezoelectric actuator of FIGS. 5A and 5B.

Please refer to FIGS. 6A to 6C. FIG. 6A schematically illustrates the front view of the structure of the piezoelectric actuator of FIGS. 5A and 5B. FIG. 6B schematically illustrates the rear view of the structure of the piezoelectric actuator of FIGS. 5A and 5B. FIG. 6C schematically illustrates the cross-sectional view of the structure of the piezoelectric actuator of FIGS. 5A and 5B. As shown in FIGS. 6A to 6C, in this embodiment, the suspension plate 1231 has a stepped structure. The suspension plate 1231 further includes a bulge 1231e disposed on the central portion 1231c of the first surface 1231a. The bulge 1231e can be a circular protrusion structure, but not limited thereto. In some embodiment, the suspension plate 1231 can be a double-sided planar square plate. Further as shown in FIG. 5C, the bulge 1231e of the suspension plate 1231 and the first surface 1232c of the outer frame 1232 are coplanar, and the first surface 1231a of the suspension plate 1231 and the first surface 1232a' of the bracket 1232a are coplanar. In addition, there is a specific depth between a top surface of the bulge 1231e of the suspension plate 1231 (or the first surface 1232c of the outer frame 1232) and the first surface 1231a of the suspension plate 1231 (or the first surface 1232a' of the bracket 1232a). As shown in FIGS. 5B and 5C, the second surface 1231b of the suspension plate 1231, the second surface 1232d of the outer frame 1232 and the second surface 1232a" of the bracket 1232a are formed as a flat coplanar structure. The piezoelectric element 1233 is attached to the flat second surface 1231b of the suspension plate 1231. In some embodiments, the suspension plate 1231 can be a double-sided planar square plate, but not limited thereto. It is adjustable according to the practical requirements. In some embodiments, the suspension plate 1231, the outer frame 1232 and the bracket 1232a may be integrally formed from a metal plate, such as, but not limited to, a stainless steel plate. Moreover, in the embodiment, the first air pump 12 further includes at least one interspace 1234 disposed among the suspension plate 1231, the outer frame 1232 and the bracket 1232a for allowing the air to pass therethrough.

Figure 7:
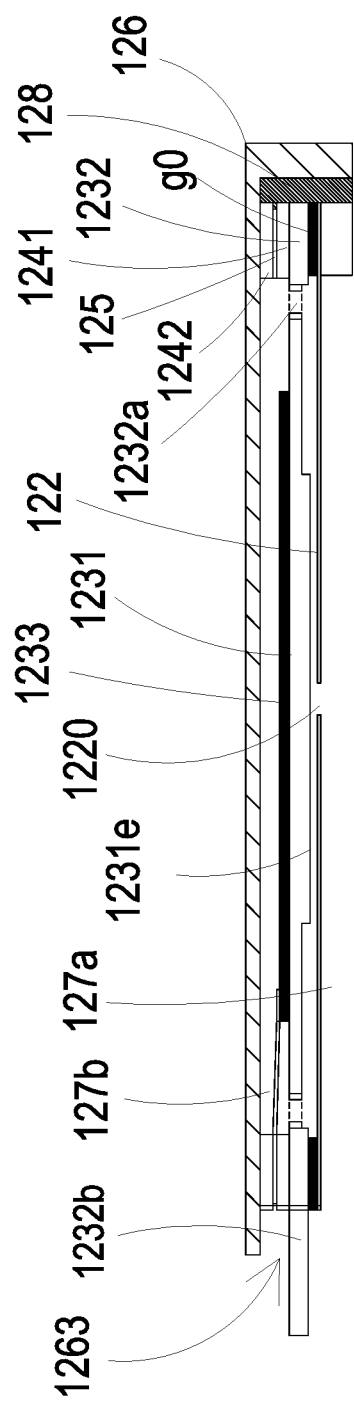
FIG. 7 schematically illustrates the cross-sectional view of the structure of the first air pump of FIGS. 5A and 5B.

Please refer to FIG. 7. FIG. 7 schematically illustrates the cross-sectional view of the structure of the first air pump of FIGS. 5A and 5B. As shown in FIG. 7, the first air pump 12 of the present disclosure includes the cover plate 126, the second insulation plate 1242, the conducting plate 125, the first insulation plate 1241, the piezoelectric actuator 123 and the resonance plate 122 stacked on each other from top to bottom sequentially. While the piezoelectric actuator 123, the first insulation plate 1241, the conducting plate 125 and the second insulation plate 1241 have been assembled and stacked, an adhesive 128 is coated around the periphery of the assembled structure to accomplish sealing. The assembled first air pump 12 is a quadrilateral structure, but not limited thereto. The shape can be adjustable according to the practical requirements. In addition, in this embodiment, only the conducting pin 1251 of the conducting plate 125 and the conducting pin 1232b (shown in FIG. 8A) of the piezoelectric actuator 123 protrude out of the cover plate 126 for electrically connecting with an external power, but not limited thereto. After gas pump 12 has been assembled, the first chamber 127b is formed between the cover plate 126 and the resonance plate 122.

In the embodiment, the first air pump 12 of the present disclosure includes a gap g0 disposed between the resonance plate 122 and the piezoelectric actuator 123, and a conductive material, for example but not limited to a conductive adhesive, is filled into the gap g0. Consequently, the depth of the gap g0 between the resonance plate 122 and the bulge 1231e of the suspension plate 1231 of the piezoelectric actuator 123 is maintained, which is capable of guiding the air to flow more quickly. Moreover, due to the proper distance between the bulge 1231e of the suspension plate 1231 and the resonance plate 122, the contact interference is reduced and the generated noise is largely reduced. In other embodiments, by adding the height of the outer frame 1232 of the piezoelectric actuator 123, the gap g0 may also be provided when the outer frame 1232 is assembled with the resonance plate 122, but the present disclosure is not limited thereto. Thus, when the piezoelectric actuator 123 is driven to perform an air collection operation, the air is guided into the opening portion 1263 of the cover plate 126 and converged to the convergence chamber 127a. Then the air flows through the central aperture 1220 of the resonance plate 122 to be temporarily stored in the first chamber 127b. When the piezoelectric actuator 123 is driven to perform a air discharge operation, the air is transferred from the first chamber 127b to the convergence chamber 127a through the central aperture 1220 of the resonance plate 122, and introduced into the first air bag 10 from the environment outside the sneaker 2.

Figure 8C:
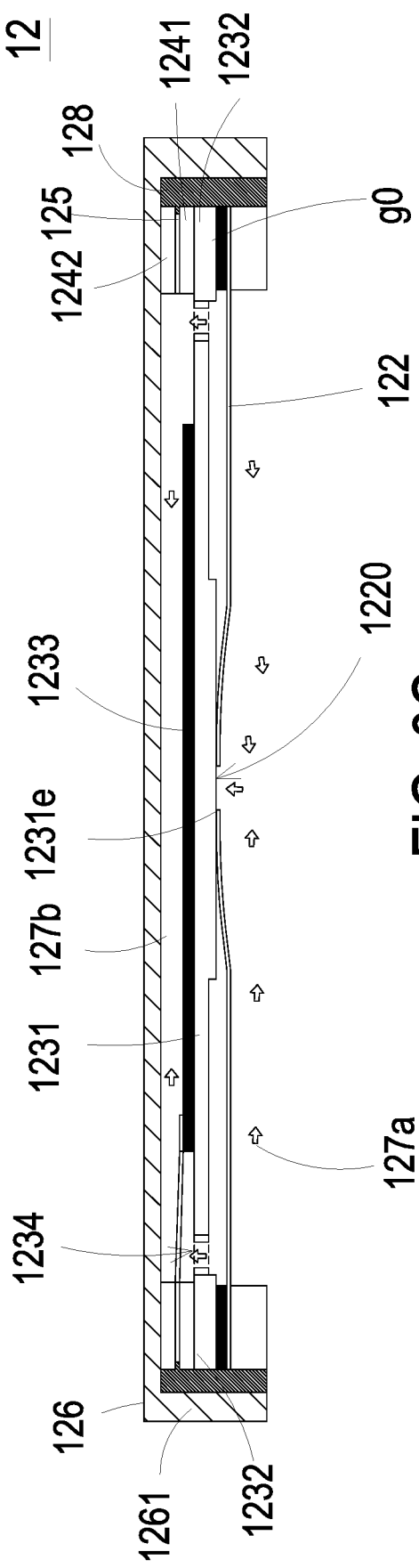

The operating process of the first air pump 12 is further described below. Please refer to FIGS. 8A to 8D. FIG. 8A to FIG. 8D schematically illustrate the actions of the first air pump according to an embodiment of the present disclosure. Firstly, as shown in FIG. 8A, the structure of the first air pump 12 is similar to that in the foregoing descriptions, being assembled by sequentially stacking and positioning the cover plate 126, the second insulation plate 1242, the conducting plate 125, the first insulation plate 1241, the piezoelectric actuator 123 and the resonance plate 122. There is a gap g0 provided between the resonance plate 122 and the piezoelectric actuator 123 so that the first chamber 127b is formed between the resonance plate 122 and the piezoelectric actuator 123. Moreover, the resonance plate 122 and the sidewalls 1261 of the cover plate 126 collaboratively define the convergence chamber 127a. When the first air pump 12 has not been driven by a voltage, the positions of the components are illustrated in FIG. 8A.

Further as shown in FIG. 8B, when the piezoelectric actuator 123 of the first pump 12 is driven by a voltage and vibrates upwardly, the air is introduced from the opening portion 1263 of the cover plate 126 into the first air pump 12 and converges to the convergence chamber 127a. Simultaneously, resonance occurs between the resonance plate 122 and the resonance of the suspension plate 1231 of the piezoelectric actuator 123 so that the resonance plate 122 undergoes a reciprocating vibration. That is, the resonance plate 122 is deformed, by which a part of the resonance plate 122 around central aperture 1220 protrudes upwardly.

Afterward, as shown in FIG. 8C, the piezoelectric actuator 123 vibrates downwardly to the original position. Meanwhile, the bulge 1231e of the suspension plate 1231 of the piezoelectric actuator 123 is close to the part of the resonance plate 122 which protrudes upwardly around central aperture 1220. It makes the air in the first air pump 12 temporarily stored in the upper half layer of the first chamber 127b.

Figure 8D:
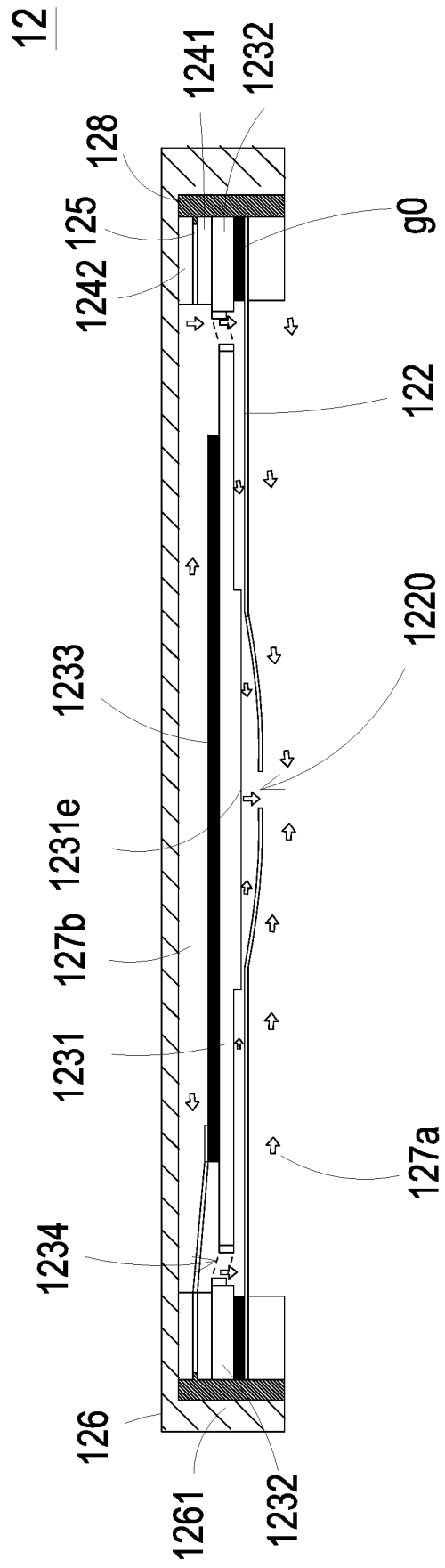

As shown in FIG. 8D, the piezoelectric actuator 123 further vibrates downwardly and the resonance plate 122 also vibrates downwardly due to the resonance of the piezoelectric actuator 123. With the downward deformation of the resonance plate 122 which shrinks the volume of the first chamber 127b, the air in the upper half layer of the first chamber 127b is pushed to flow toward the both sides and pass through the interspace 1234 of the piezoelectric actuator 123 downwardly, so as to be transferred to the central aperture 1220 of the resonance plate 122 and compressed to be discharged. In the aspect of this embodiment, when the resonance plate 122 performs the vertical reciprocating vibration, the gap g0 between the resonance plate 122 and the piezoelectric actuator 123 may help to increase the maximum displacement along the vertical direction during its vibration. In other words, the configuration of the gap g0 provided between the resonance plate 122 and the piezoelectric actuator 123 allows the resonance plate 122 to vibrate at a greater amplitude when resonance occurs.

Finally, the resonance plate 122 returns to the original position as shown in FIG. 8A. As described above, the operations of FIGS. 8A to 8D may be repeatedly performed, so that the air is fed from the opening portion 1263 of the cover plate 126 into the convergence chamber 127a and flows to the first chamber 127b. Afterward, the air is further transferred from the first chamber 127b to the convergence chamber 127a, and the air flows from the environment outside the sneaker 2 into the first air bag 10 stably. In other words, when the first air pump 12 of the present disclosure is operated, the air flows through the opening portion 1263 of the cover plate 126, the convergence chamber 127a, the first chamber 127b, the convergence chamber 127a and the first air bag 10 sequentially. Accordingly, the first air pump 12 of the present disclosure provides a single component (i.e., the cover plate 126), which utilizes the structural design of the opening portion 1263 of the cover plate 126, so that the number of components of the first air pump 12 can be reduced, and the entire process can be simplified.

Figure 9A:
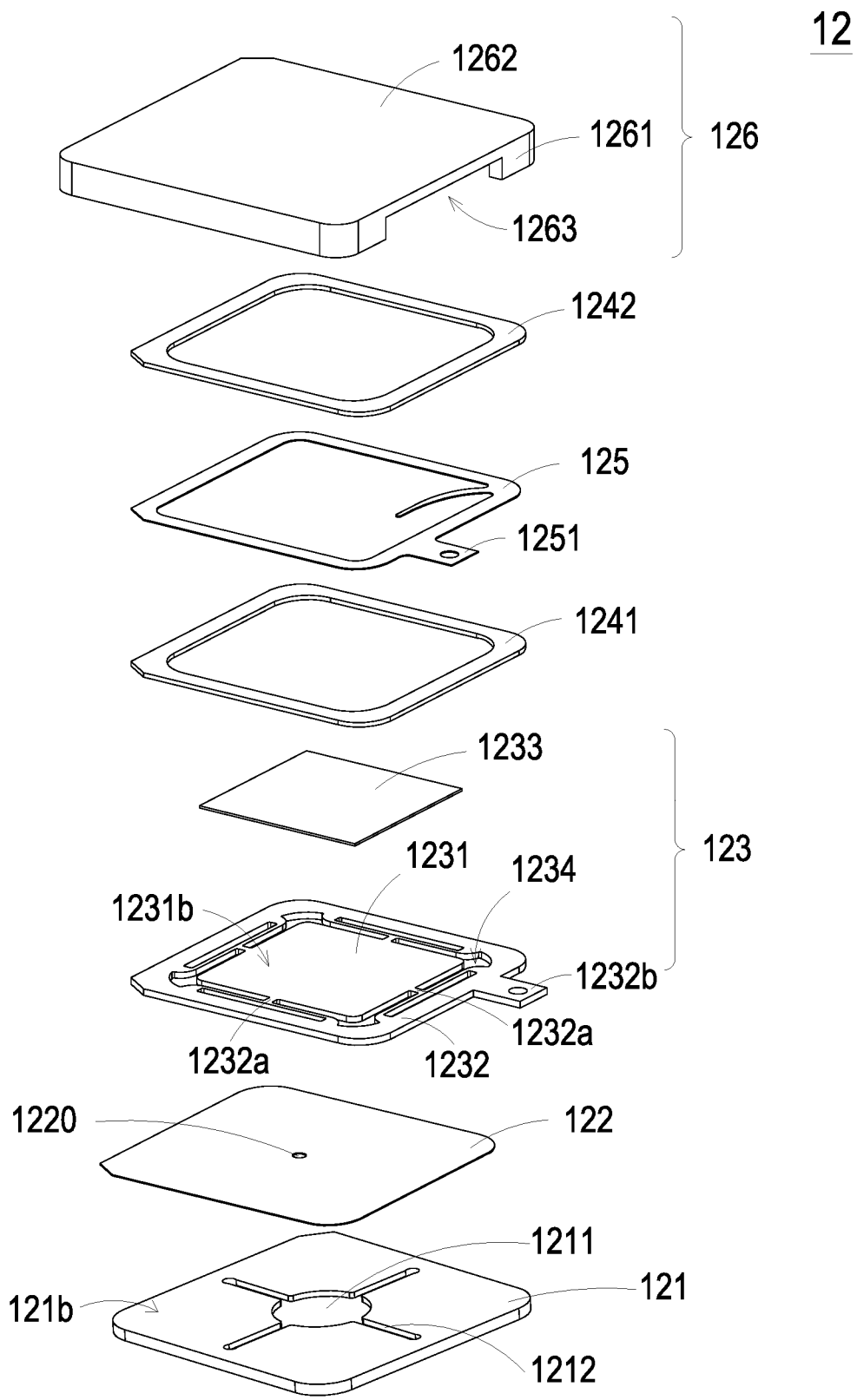
FIGS. 9A and 9B respectively schematically illustrate different views of the exploded structure of the first air pump according to another embodiment of the present disclosure.
Figure 9B:
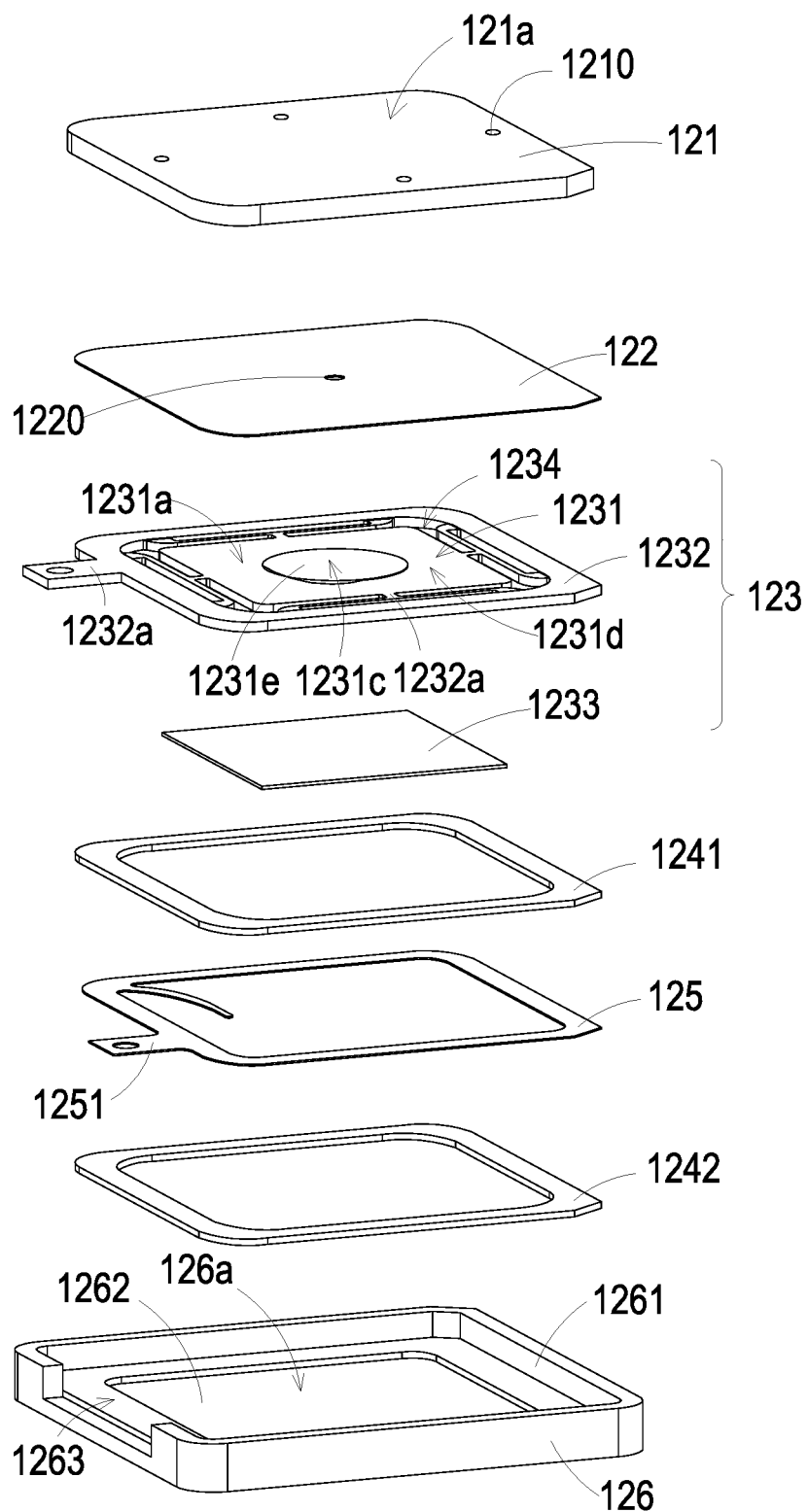

Please refer FIGS. 9A and 9B. FIGS. 9A and 9B respectively schematically illustrate different views of the exploded structure of the first air pump according to another embodiment of the present disclosure. In the embodiment, the first air pump 12 includes the cover plate 126, the second insulation plate 1242, the conducting plate 125, the first insulation plate 1241, the piezoelectric actuator 123 and the resonance plate 122 stacked on each other sequentially. Structures, elements and configurations of the first air pump 12 are similar to those of the embodiments described above and are not redundantly described herein. In the embodiment, the first air pump 12 further includes an inlet plate 121. The inlet plate 121 is aligned with the resonance plate 122 and stacked thereon. The inlet plate 121 includes a first surface 121a, a second surface 121b and at least one inlet 1210. In the embodiment, the inlet plate 121 has four inlets 1210, but not limited thereto. The inlets 1210 runs through the first surface 121a and the second surface 121b, so that the air is fed into the first air pump 12 through the at least one inlet 1210 in response to the action of the atmospheric pressure. In addition, as shown in FIG. 9B, the inlet plate 121 includes at least one convergence channel 1212 disposed on the first surface 121a and spatially corresponding to the at least one inlet 1210 on the second surface 121b of the inlet plate 121. There is a central cavity 1211 formed at the intersection of those convergences channels 1212. The central cavity 1211 is in communication with the convergence channels 1212. Thus, the air fed into the convergence channels 1212 through the at least one inlet 1210 can be converged and transferred to the central cavity 1211. As a result, the air is effectively converged to the central aperture 1220 of the resonance plate 122 and transferred to the interior of the first air pump 12. The inlet plate 121 is a single structure integrally composed of the inlets 1210, the convergence channels 1212 and the central cavity 1211. The convergence chamber is formed within the central cavity 1211 for storing the air temporarily. In some embodiment, the material of the inlet plate 121 can be for example but not limited to the stainless steel. In other embodiments, the depth of the convergence chamber formed within the central cavity 1211 and the depth of those convergence channels 1212 are equal, but not limited herein. The resonance plate 122 can be made of for example but not limited to a flexible material. Moreover, the resonance plate 122 has a central aperture 1220 corresponding to the central cavity 1211 on the second surface 121b of the inlet plate 121, so as to allow the air to flow therethrough downwardly. In other embodiments, the resonance plate 122 can be made of for example but not limited to a copper material.

According to the above description, through the operation of the first air pump 12, the air is introduced into the first air bag 10 from the environment outside the sneaker 2, so that the interior of the first air bag 10 is filled with air and the pressure thereof is increased, thereby providing sufficient supporting force and cushioning capacity to the use's front foot sole. Similarly, the structure and the operation of the second air pump 13 are identical to those of the first air pump 12. Through the operation of the second air pump 13, the air is introduced into the second air bag 11 from the environment outside the sneaker 2, so that the interior of the second air bag 11 is filled with air and the pressure thereof is increased, thereby providing sufficient supporting force and cushioning capacity to the use's rear foot sole. Accordingly, imbalance of the front foot sole and rear foot sole is avoided, and the comfort of overall wearing is significantly enhanced.

From the above descriptions, the present disclosure provides a dynamic pressure controlled air cushion device disposed on a sole. By inflating or exhausting the first air bag and the second air bag, the supporting force for the user's front foot sole and rear foot sole is adjusted, so that the difference in exerted forces between the user's front foot sole and rear foot sole is balanced, the comfort of overall wearing is enhanced, and injuries are avoided. The dynamic pressure controlled air cushion device further includes a first sensor and a second sensor for sensing the force exerted by the foot, so as to be adjustable according to different user's habits of exerting force, thereby adjusting to the best service condition for the user. The dynamic pressure controlled air cushion device further includes a first non-return valve and a second non-return valve for controlling the air entering and exiting the first air bag and the second air bag, so as to enhance the stability of the sneaker when wearing it. The dynamic pressure controlled air cushion device further includes a manual control function or a remote control function, so that the user may adjust the dynamic pressure controlled air cushion device of each sole through manual control or remote control for the most comfortable fit.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A dynamic pressure controlled air cushion device applied to a shoe, the shoe comprising a bottom part and the dynamic pressure controlled air cushion device comprising:
   a first air bag disposed on the bottom part and disposed corresponding to a front foot sole of a user;
   a second air bag disposed on the bottom part and disposed corresponding to a rear foot sole of the user;
   an air passage communicated between the first air bag and the second air bag;
   a first air pump disposed and enclosed in the air passage;
   a second air pump disposed and enclosed in the air passage;
   a first sensor disposed on the bottom part and disposed adjacent to the first air bag;
   a second sensor disposed on the bottom part and disposed adjacent to the second air bag; and
   a control module electrically connected with the first air pump, the second air pump, the first sensor and the second sensor;
   wherein when the first sensor senses that a force exerted by the front foot sole of the user is larger than a specific first load value interval, the first sensor sends a first sensing signal to the control module, and the control module enables the first air pump according to the first sensing signal, so that air is introduced into the first air bag by the first air pump, and the first air bag is inflated to increase a supporting force for the front foot sole of the user, and wherein when the second sensor senses that a force exerted by the rear foot sole of the user is larger than a specific second load value interval, the second sensor sends a second sensing signal to the control module, and the control module enables the second air pump according to the second sensing signal, so that the air is introduced into the second air bag by the second air pump, and the second air bag is inflated to increase a supporting force for the rear foot sole of the user.

2. The dynamic pressure controlled air cushion device according to claim 1, wherein when the first sensor senses that the force exerted by the front foot sole of the user reaches the specific first load value interval, the first sensor sends a first disabling signal to the control module, and the control module controls the first air pump to stop operating according to the first disabling signal, and wherein when the second sensor senses that the force of the rear foot sole of the user reaches the specific second load value interval, the second sensor sends a second disabling signal to the control module, and the control module controls the second air pump to stop operating according to the second disabling signal.

3. The dynamic pressure controlled air cushion device according to claim 2, wherein the first air pump further comprises a first non-return valve, which is a switchable valve structure, wherein when the first air pump stops operating, the air passage is closed by the first non-return valve for preventing the air in the first air bag from backflow, and wherein when the first sensor senses that the force exerted by the front foot sole of the user is less than the specific first load value interval, the first sensor sends a first decompressing signal to the control module, and the control module enables the first non-return valve according to the first decompressing signal, so that the first non-return valve is opened, the air is discharged from the first air bag, and the first air bag exhausts to decrease the supporting force for the front foot sole of the user.

4. The dynamic pressure controlled air cushion device according to claim 2, wherein the second air pump further comprises a second non-return valve, which is a switchable valve structure, wherein when the second air pump stops operating, the air passage is closed by the second non-return valve for preventing the air in the second air bag from backflow, and wherein when the second sensor senses that the force of the rear foot sole of the user is less than the specific second load value interval, the second sensor sends a second decompressing signal to the control module, and the control module enables the second non-return valve according to the second decompressing signal, so that the second non-return valve is opened, the air is discharged from the second air bag, and the second air bag exhausts to decrease the supporting force for the rear foot sole of the user.

5. The dynamic pressure controlled air cushion device according to claim 1, wherein the first sensor and the second sensor are both load sensors, so as to directly sense changes of weight around the first air bag and the second air bag, respectively.

6. The dynamic pressure controlled air cushion device according to claim 1, wherein the first sensor and the second sensor are both air pressure sensors, the first sensor is in communication with an interior of the first air bag, and the second sensor is in communication with an interior of the second air bag, so as to directly sense changes of air pressure in the first air bag and the second air bag generated by the force of a foot of the user, respectively.

7. The dynamic pressure controlled air cushion device according to claim 1, wherein the air passage further comprises an external passage, wherein the air passage is in communication with an environment outside the shoe through the external passage, so that the air is introduced from the environment outside the shoe to the first air bag by the first air pump, and the air is introduced from the outside of the shoe to the second air bag by the second air pump.

8. The dynamic pressure controlled air cushion device according to claim 1, wherein the dynamic pressure controlled air cushion device further comprises a manual adjustment device, and the manual adjustment device is a button, a switch or a remote control device.

9. The dynamic pressure controlled air cushion device according to claim 1, wherein the first air pump and the second air pump are both piezoelectric air pumps, and the piezoelectric air pump comprises:
 a resonance plate having a central aperture and a movable part, wherein the movable part surrounds the central aperture;
 a piezoelectric actuator disposed corresponding to the resonance plate; and
 a cover plate having at least one sidewall, a bottom plate and an opening portion, wherein the at least one sidewall surrounds and protrudes vertically from a periphery of the bottom plate and an accommodation space is defined by the bottom plate and the at least one sidewall collaboratively, wherein the resonance plate and the piezoelectric actuator are accommodated within the accommodation space, and the opening portion is disposed on the sidewall;
 wherein a chamber is formed between the resonance plate and the piezoelectric actuator spaced apart by a gap, wherein when the piezoelectric actuator is enabled, the air is guided into the opening portion of the cover plate, transferred through the central aperture of the resonance plate, and introduced into the chamber, wherein the air is further transferred through a resonance between the piezoelectric actuator and the movable part of the resonance plate.

10. The dynamic pressure controlled air cushion device according to claim 9, wherein the piezoelectric actuator comprises:
 a suspension plate having a first surface and a second surface, wherein the suspension plate is permitted to undergo a bending vibration;
 an outer frame arranged around the suspension plate;
 at least one bracket connected between the suspension plate and the outer frame for elastically supporting the suspension plate; and
 a piezoelectric element, wherein a length of a side of the piezoelectric element is smaller than or equal to a length of a side of the suspension plate, and the piezoelectric element is attached on the first surface of the suspension plate, wherein when a voltage is applied to the piezoelectric element, the suspension plate is driven to undergo the bending vibration.

11. The dynamic pressure controlled air cushion device according to claim 10, wherein the suspension plate is a square suspension plate with a bulge.

12. The dynamic pressure controlled air cushion device according to claim 10, wherein the piezoelectric air pump further comprises a conducting plate, a first insulation plate and a second insulation plate, wherein the resonance plate, the piezoelectric actuator, the first insulation plate, the conducting plate, the second insulation plate and the cover plate are stacked on each other sequentially.

13. The dynamic pressure controlled air cushion device according to claim 12, wherein the piezoelectric actuator further comprises an inlet plate, and the inlet plate is aligned with the resonance plate and stacked thereon, wherein the inlet plate comprises a first surface, a second surface, at least one inlet, a central cavity and at least one convergence channel, wherein the at least one inlet runs through the first surface and the second surface, the at least one convergence channel is formed on the second surface and in communication with the at least one inlet, the central cavity is formed on the second surface and spatially corresponding to the central aperture of the resonance plate, and the central cavity is in communication with the at least one convergence channel, wherein after the air is introduced into the at least one inlet, the air is converged and transferred to the central cavity along the at least one convergence channel, so as to transfer the air to the central aperture of the resonance plate.

14. The dynamic pressure controlled air cushion device according to claim 1, wherein the dynamic pressure controlled air cushion device further comprises a battery module for supplying electrical energy to the control module.

15. The dynamic pressure controlled air cushion device according to claim 1, wherein the control module further comprises a wireless signal transmission and receiving unit for transmitting or receiving a data signal.

16. The dynamic pressure controlled air cushion device according to claim 15, wherein the wireless signal transmission and receiving unit transmits signals via infrared, Bluetooth or WIFI.

* * * * *